United States Patent [19]
Bodor

[11] Patent Number: 5,231,089
[45] Date of Patent: Jul. 27, 1993

[54] METHOD OF IMPROVING ORAL BIOAVAILABILITY OF CARBAMAZEPINE

[75] Inventor: Nicholas S. Bodor, Gainesville, Fla.

[73] Assignee: University of Florida, Gainesville, Fla.

[21] Appl. No.: 907,178

[22] Filed: Jul. 1, 1992

Related U.S. Application Data

[63] Continuation of Ser. No. 801,428, Dec. 2, 1991, abandoned.

[51] Int. Cl.$^5$ .................. A61K 31/70; C08B 37/16
[52] U.S. Cl. .................. 514/58; 514/277; 514/279; 514/964; 536/103; 424/464; 424/468
[58] Field of Search .............. 514/58, 277, 279, 964; 536/103; 424/464, 468

[56] References Cited

U.S. PATENT DOCUMENTS

| | | | |
|---|---|---|---|
| 4,727,064 | 2/1988 | Pitha | 514/58 |
| 4,764,604 | 8/1988 | Müller | 536/103 |
| 4,983,586 | 1/1991 | Bodor | 514/58 |
| 5,024,998 | 6/1991 | Bodor | 514/58 |
| 5,051,406 | 9/1991 | Satoh | 514/776 |

OTHER PUBLICATIONS

*Pharmaceutical Research,* vol. 8, No. 10, Oct. 1991 (Supplement), Abstract PDD7038 (Choudhury et al.).
Brewster et al., *J. Pharm. Sci.,* vol. 80, No. 4, Apr. 1991.
*Pharmaceutical Research,* vol. 8, No. 10, Oct. 1991 (Supplement), abstract PDD7038 (Choudhury et al.).
Morselli, Chapter 33 in *Antiepileptic Drugs,* Third Edition, ed. R. Levy et al., Raven Press, Ltd., New York, 1989, pp. 473–490.
*The Pharmacological Basis of Therapeutics,* ed. Louis S. Goodman and Alfred Gilman, fifth edition, MacMillan Publishing Co., Inc. New York, 1975, p. 211.
Monaco et al., *J. Int. Med. Res.* 12 (1984), pp. 108–113.
Eadie et al., *The Medical Journal of Australia,* vol. 146, Mar. 16, 1987, pp. 313–316.
Bloomer et al., *Clinical Pharmacy,* vol. 6, Aug. 1987, pp. 646–649.
Maas et al., *Therapeutic Drug Monitoring* 9, (1987), pp. 28–33.
Graves et al., *Epilepsia,* 24 (1983), pp. 604–608.
Neuvonen et al., *Br. J. Clin. Pharmac.* 24 (1987), pp. 839–841.
Gérardin et al., *Epilepsia* 31 (3), (1990), pp. 334–338.

*Primary Examiner*—Ronald W. Griffin

[57] ABSTRACT

The invention provides a method for improving the oral bioavailability of carbamazepine by administering per os, to a warm-blooded animal in need of carbamazepine therapy, a therapeutically effective amount of carbamazepine complexed with cyclodextrin selected from the group consisting of hydroxypropyl and hydroxyethyl derivatives of β- and γ-cyclodextrin.

35 Claims, 2 Drawing Sheets

Fig. 2

METHOD OF IMPROVING ORAL BIOAVAILABILITY OF CARBAMAZEPINE

This application is a continuation of application Ser. No. 07/801,428, filed Dec. 2, 1991, now abandoned.

FIELD OF THE INVENTION

The present invention relates to a method of improving the oral bioavailability of carbamazepine using complexes of the drug with selected cyclodextrin derivatives, and to compositions useful in the subject method.

BACKGROUND OF THE INVENTION

Carbamazepine, or 5H-dibenz[b,f]azepine-5-carboxamide, is a widely used anticonvulsant agent having the structural formula It is available in the U.S. as Tegretol ® brand chewable tablets of 100 mg, tablets of 200 mg and suspension of 100 mg/5 mL, intended for oral administration as an anticonvulsant or as a specific analgesic for trigeminal neuralgia. Recommended maintenance dosage levels in adults and children over 12 years of age are 800-1200 mg daily, although up to 1600 mg daily have been used in adults. In children of 6 to 12 years of age, the maintenance dosage level is usually 400-800 mg daily.

For complex partial seizures (temporal lobe, psychomotor), carbamazepine is considered the anticonvulsant drug of choice. It is also of proven efficacy in the treatment of generalized tonic-clonic seizures (grand mal). In addition, carbamazepine has been used in treating simple partial (focal, Jacksonian) seizures and in patients with mixed seizure patterns which include the above, or other partial or generalized seizures. It is not used in the treatment of absence seizures (petit mal).

In addition to its proven effectiveness, carbamazepine has, in many respects, a more favorable profile in terms of the incidence and severity of side-effects than other anticonvulsants. Thus, carbamazepine is less sedating and causes less intellectual function impairment than other antiepileptic drugs such as phenobarbital, primidone and phenytoin. Furthermore, carbamazepine does not precipitate gingival hypertropy, hirsutism, acne or other undesired effects associated with phenytoin. These attributes have helped to make carbamazepine the drug of choice in women and children.

Nevertheless, carbamazepine usage is not without its difficulties. The drug should, in general, not be used in combination with other drugs because of dangerous drug interactions. Therapeutic plasma levels of carbamazine range from about 4 to 10 $\mu$g/mL, but adverse effects are generally encountered in about 50% of patients with serum carbamazepine levels of 8.5 to 10 $\mu$g/mL. Thus, the therapeutic index is not large. Such adverse effects as diplopia, dizziness, drowsiness and ataxia occur above 6 $\mu$g/mL, and nystagmus may occur at serum levels below the therapeutic range. Anorexia, nausea, rash (including Stevens-Johnson syndrome), edema, aplastic anemia, agranulocytosis, thrombocytopenia and transient leukopenia may also occur. The most severe effects are those which have been observed in the hemopoietic system, the skin and the cardiovascular system, some of which have resulted in fatalities.

Carbamazepine has been used as an anticonvulsant agent for over 20 years. During that time, a number of workers have studied the absorption characteristics, including the bioavailability, of carbamazepine from various formulations thereof. From Morselli, Chapter 33 in *Antiepileptic Druge, Third Edition,* ed. R. Levy et al, Raven Press, Ltd., N.Y., 1989, 473-490, and references cited therein, it appears to be widely recognized that the oral absorption of carbamazepine is slow and somewhat erratic. It is equally widely recognized, however, that oral absorption is adequate; see, for example, *The Pharmacological Basis of Therapeutics,* ed. Louis S. Goodman and Alfred Gilman, fifth edition, MacMillan Publishing Co., Inc., N.Y., 1975, page 211.

Relative total bioavailabilities reported for various carbamazepine formulations appear to be relatively constant, although rates of absorption may differ.

Monaco et al, *J. Int. Med. Res.* 12 (1984), 108-113, found no difference in plasma levels when carbamazepine was given to epileptic patients in 200 or 400 mg tablets, and indicated that their data supported the similar bioavailability of 200 mg and 400 mg carbamazepine tablets during chronic administration to epileptic patients.

Eadie et al, *The Medical Journal of Australia,* Vol. 146, Mar. 16, 1987, 313-316, found differences in absorption rates between tablets available in Australia in 1977 and those available since 1980, but no significant difference in total bioavailability (area under the curve). The authors attributed any discrepancies between earlier Australian reports and European data relating to bioavailability to a reduced absorption rate of Australian carbamazepine before 1980, and noted that the non-Australian workers had not questioned the bioavailability of the drug in the preparations they tested, although no intravenous preparation was available for comparison.

The relative bioavailability of an extemporaneous carbamazepine oral suspension relative to that of the tablet used in its manufacture was reported by Bloomer et al, *Chemical Pharmacy,* Vol. 6, Aug. 1987, 646-649. Although the mean time to maximum concentration was significantly shorter after suspension than after tablet administration, there was no significant difference in the extent of absorption. Mean ($\pm$S.D.) bioavailability of the suspension relative to the tablet was 94.46% $\pm$ 20.42. The authors indicated these findings to be similar to those of similar studies of the commercial carbamazepine oral suspension.

Maas et al, *Therapeutic Drug Monitoring* 9, 28-33 (1987), have described a comparative bioavailability study of carbamazepine tablets and a chewable tablet formulation. Although the authors noted that carbamazepine "is relatively water insoluble and oral absorption is erratic, with great variability in absorption rates noted between individuals and between various oral formulations", no significant differences in the bioavailability between carbamazepine 200 mg tablets and an equivalent dose of chewable tablets were found in their study. Statistically significant differences in peak plasma concentrations were found but the clinical significance was deemed minimal and the two types of tablets were concluded to be interchangeable.

Graves et al, *Epilepsia*, 24 (1983), 604–608, studied the bioavailability of rectally administered carbamazepine suspension in dogs. Doses of 20 mg/kg were given to dogs as oral tablet, oral suspension and rectal suspension. No significant difference in total absorption was noted between the oral and rectal suspensions. Rectal administration was found to produce a prolonged, though complete, absorption profile relative to the oral suspension. Neuvonen et al, *Br. J. clin. Pharmac.* 24 (1987), 839–841, in studies of healthy human subjects, made essentially the same finding, i.e. that absorption was significantly slower after the rectal than after the oral route, but the total bioavailability was similar.

Because of the lack of an injectable formulation for carbamazepine, there has not been precise information relating to the drug's absolute bioavailability. Values estimated from studies using $^{14}$C-labeled carbamazepine have ranged from 75% to 85%. See Morselli, Chapter 33 in *Antiepileptic Drugs, Third Edition*, ed. R. Levy et al, Raven Press, Ltd., N.Y., 1989, 473–490, particularly page 474 and the Faigle et al reference cited therein. Very recently, Gérardin et al, in *Epilepsia*, 31(3), 1990, 334–338, have reported on the absolute bioavailability of carbamazepine after oral administration of a 2% syrup. Healthy male volunteers were given 100 mg of carbamazepine as a intravenous infusion and 100 mg of 15N-labeled carbamazepine as a 2% oral suspension, concomitantly. Comparison of the areas under the plasma curves (AUC) obtained by the two routes of administration showed the bioavailability of carbamazepine from the oral suspension to be equivalent to its bioavailability when administered intravenously. Absolute bioavailability of carbamazepine administered as the oral suspension was calculated as 102.3% and 100.1% for subjects 1 and 2, respectively.

Thus, the consensus in the art has been to the effect that the total oral bioavailability of carbamazepine is highly acceptable and leaves little, if any, room for improvement. The most improvement in oral bioavailability possible based on the carbamazepine literature would appear to be approximately 18–33%, a very modest increase which, even if attainable, would likely not warrant reformulation of existing compositions.

Cyclodextrins are cyclic oligosaccharides. The most common cyclodextrins are α-cyclodextrin, which is composed of a ring of six glucose residues; β-cyclodextrin, which is composed of a ring of seven glucose residues; and γ-cyclodextrin, which is composed of a ring of eight glucose units. The inside cavity of a cyclodextrin is lipophilic, while the outside of the cyclodextrin is hydrophilic; this combination of properties has led to widespread study of the natural cyclodextrins, particularly in connection with pharmaceuticals, and many inclusion complexes have been reported. β-Cyclodextrin has been of special interest because of its cavity size, but its relatively low aqueous solubility (about 1.8% w/v at 25° C.) and attendant nephrotoxicity have limited its use in the pharmaceutical field.

Attempts to modify the properties of the natural cyclodextrins have resulted in the development of heptakis (2,6-di-O-methyl)-β-cyclodextrin, heptakis (2,3,6-tri-O-methyl)-β-cyclodextrin, hydroxypropyl-β-cyclodextrin, β-cyclodextrin-epichlorohydrin polymer and others. For a comprehensive review of cyclodextrins and their use in pharmaceutical research, see Pitha et al, in *Controlled Drug Delivery*, ed. S.D. Bruck, Vol. I, CRC Press, Boca Raton, Fla., 125-148 (1983). For an even more recent overview, see Uekama et al, in *CRC Critical Reviews in Therapeutic Drug Carrier Systems*, Vol. 3 (1), 1–40 (1987); Uekama, in *Topics in Pharmaceutical Sciences* 1987, eds. D. D. Breimer and P. Speiser, Elsevier Science Publishers B.V. (Biomedical Division), 1987, 181–194; and Pagington, *Chemistry in Britain*, May 1987, 455–458.

Inclusion complexes of α-, β- or γ-cyclodextrin or their mixtures with a variety of drugs have been described by numerous parties and various advantages have been attributed to the complexes. These descriptions include those documents summarized in Bodor U.S. Pat. Nos. 4,983,586 and 5,024,998, incorporated by reference herein in their entireties and relied upon.

Inclusion complexes of 2,6-di-0-methyl-β-cyclodextrin with dibenzo[bd]pyran derivatives and salts having analgesic, antemetic and narcosis-potentiating activities have been described in Nogradi et al U.S. Pat. No. 4,599,327; increased water solubility and thus improved biological activity have been claimed for the complexes. A review of the pharmaceutical applications of such methylated cyclodextrins has been published by Uekama, *Pharm. Int.*, Mar. 1985, 61–65; see also Pitha, *Journal of Inclusion Phenomena* 2, 477–485 (1984).

Cyclodextrin polymer has been reported by Fenyvesi et al, *Chem. Pharm. Bull.* 32 (2), 665–669 (1984) to improve the dissolution of furosemide. Improvements in the dissolution and absorption of phenytoin using a water-soluble β-cyclodextrin epichlorohydrin polymer have been described by Uekama et al, *International Journal of Pharmaceutics*, 23, 35–42 (1985).

Hydroxypropyl-β-cyclodextrin and its preparation by propylene oxide addition to β-cyclodextrin were described in Gramera et al U.S. Pat. No. 3,459,731 approximately 20 years ago. (Gramera et al also described the analogous preparation of hydroxyethyl-β-cyclodextrin by ethylene oxide reaction with β-cyclodextrin.) Much more recently recently, Pitha and coworkers have described the improved preparation of this cyclodextrin derivative and its effects on the dissolution of various drug molecules. See Pitha U.S. Pat. No. 4,596,795, dated Jun. 24, 1986. Success with other cyclodextrins, including poly-γ-cyclodextrin and hydroxypropyl-γ-cyclodextrin, have also been noted in the Pitha patent. See also Pitha et al, *J. Pharm. Sci.*, Vol. 74, No. 9, Sep. 1985, 987–990, concerning the same and related studies.

The improved, optimized preparation and purification of hydroxypropyl-β-cyclodextrin has been described by Pitha et al, *International Journal of Pharmaceutics*, 29, 73–82 (1986). In the same publication, the authors have described increased water solubility for 32 drugs in concentrated (40 to 50%) aqueous solutions of hydroxypropyl-β-cyclodextrin. The authors indicated this to be an extension of their earlier work with hydroxypropyl-β-cyclodextrin, which was previously found effective for oral administration of the sex hormones to humans. Their later work reported in Pitha et al, *International Journal of Pharmaceutics*, 29, 73–82 (1986), has also been described in Pitha U.S. Pat. No. 4,727,064, dated Feb. 23, 1988. That patent claims a composition containing an amorphous complex of cyclodextrin and a drug, and a method of producing a stabilizing amorphous complex of a drug and a mixture of cyclodextrins comprising (1) dissolving an intrinsically amorphous mixture of cyclodextrin derivatives which are water soluble and capable of forming inclusion complexes with drugs in water; and (2) solubilizing lipophilic drugs into aqueous media to form a solution and form a solubilized drug/cyclodextrin complex. The patent describes the preparation of various substituted amorphous cyclodextrins, including hydroxypropyl-$\beta$-cyclodextrin and hydroxypropyl-$\gamma$-cyclodextrin, the latter by analogous condensation of propylene oxide and $\gamma$-cyclodextrin.

Uekama et al, *CRC Critical Reviews in Therapeutic Drug Carrier Systems*, Vol. 3 (1), 1–40 (1987), have described the characteristics of various cyclodextrins, including hydroxypropyl-$\beta$-cyclodextrin. The authors have presented data showing improved solubilization in water in the presence of 15 mg/mL of hydroxypropyl-$\beta$-cyclodextrin for the drugs carmofur, diazepam, digitoxin, digoxin, flurbiprofen, indomethacin, isosorbide dinitrate, phenytoin, prednisolone, progesterone and testosterone. The authors have further indicated that parenteral administration of large doses of cyclodextrins should be avoided, but that "$\gamma$-cyclodextrin and hydroxypropyl-$\beta$-cyclodextrin seem to be useful in drug solubilization for injections and liquid preparations used for mucous membranes."

JANSSEN PHARMACEUTICAL N.V.'s International Patent Application No. PCT/EP84/00417, published under International Publication No. W085/02767 on Jul. 4, 1985, has described pharmaceutical compositions comprising inclusion compounds of drugs, which are unstable or only sparingly soluble in water, with partially etherified $\beta$-cyclodextrin derivatives having hydroxyalkyl and optionally additional alkyl groups. Among the cyclodextrin derivatives contemplated is hydroxypropyl-$\beta$-cyclodextrin, while the drugs include nonsteroidal anti-rheumatic agents, steroids, cardiac glycosides and derivatives of benzodiazepine, benzimidazole, piperidine, piperazine, imidazole and triazole.

The preparation of amorphous water-soluble cyclodextrin derivatives, including 2-hydroxyethyl-$\beta$-cyclodextrin, 3-hydroxypropyl-$\beta$-cyclodextrin and 2-hydroxypropyl-$\gamma$-cyclodextrin, is described by Irie et al, *Pharmaceutical Research*, Vol. 5, No. 11, 1988, 713–717. That report also addresses the distribution of the substituents among the glucose residues of the cyclodextrin ring.

A pharmaceutical evaluation of hydroxyalkyl ethers of $\beta$-cyclodextrin has been reported by Yoshida et al, *International Journal of Pharmaceutics* 46, 1988, 217–222. Aqueous solubilities, surface activities, hemolytic activity and local irritancy are reported. The data suggest that hydroxyalkyl-$\beta$-cyclodextrins overcome many of the undesirable characteristics of $\beta$-cyclodextrin usage in pharmaceuticals.

JANSSEN PHARMACEUTICA N.V.'s European Patent Application No. 86200334.0, published under EPO Publication No 0197571 on Oct. 15, 1986, describes $\gamma$-cyclodextrin derivatives which are $\gamma$-cyclodextrin substituted with $C_1$–$C_6$ alkyl, hydroxy $C_1$–$C_6$ alkyl, carboxy $C_1$–$C_6$ alkyl or $C_1$–$C_6$ alkyloxycarbonyl $C_1$–$C_6$ alkyl or mixed ethers thereof. Among the specific derivatives named are hydroxypropyl-$\gamma$-cyclodextrin and hydroxyethyl-$\gamma$-cyclodextrin. Compositions comprising the cyclodextrin derivatives and a drug are also described. See also corresponding Muller U.S. Pat. No. 4,764,604, dated Aug. 16, 1988.

Uekama, in *Topics in Pharmaceutical Sciences* 1987, eds. D. D. Breimer and P. Speiser, Elsevier Science Publishers B.V. (Biomedical Division), 1987, 181–194, has described the effects on bio-pharmaceutical properties of maltosyl and glucosyl cyclodextrin derivatives, as well as hydroxypropyl and other hydrophilic cyclodextrin derivatives, including enhanced drug absorption. The mechanism of enhancing drug absorption is described and the apparent stability constants for inclusion complexes of various drugs with $\beta$-cyclodextrin, dimethyl-$\beta$-cyclodextrin, hydroxypropyl-$\beta$-cyclodextrin and maltosyl-$\beta$-cyclodextrin are given. Drugs studied with these cyclodextrins include benoxaprofen, biphenyl acetic acid, carmofur, clofibrate, chlorpromazine, diazepam, diclofenac, digitoxin, digoxin, ethyl 4-biphenyl acetate, flurbiprofen, isosorbide dinitrate, indomethacin, menadione, nimodipine, nisoldipine, phenytoin, prednisolone, progesterone, prostacyclin, various prostaglandins ($E_1$, $E_2$, $A_1$, $A_2$), protriptyline, spironolactone and testosterone.

Bodor U.S. Pat. Nos. 5,002,935, issued Mar. 26, 1991, and 5,017,566, issued May 21, 1991, relate to stabilizing the reduced, dihydropyridine forms of dihydropyridine$\rightleftarrows$pyridinium salt redox systems for brain-targeted drug delivery by complexation with cyclodextrin selected from the group consisting of hydroxypropyl, hydroxyethyl, glucosyl, maltosyl and maltotriosyl derivatives of $\beta$- and $\gamma$-cyclodextrins. The complexes also provide a means for increasing the ratio of initial brain to lung concentrations of drug, leading to decreased toxicity. In selected instances, improved water solubilities are noted as well.

Bodor U.S. Pat. Nos. 4,983,586, issued Jan. 8, 1991, and 5,024,998, issued Jun. 18, 1991, relate to pharmaceutical formulations for parenteral use. Aqueous parenteral solutions of drugs which are insoluble or only sparingly soluble in water and/or which are unstable in water, combined with cyclodextrin selected from the group consisting of hydroxypropyl, hydroxyethyl, glucosyl, maltosyl and maltotriosyl derivatives of $\beta$- and $\gamma$-cyclodextrins, provide a means for alleviating problems associated with drug precipitation at the injection site and/or in the lungs or other organs following parenteral administration. The parenteral solutions contain from about 20% to about 50% of the selected cyclodextrin(s). The drugs may be the dihydropyridine forms of dihydropyridine$\rightleftarrows$ pyridinium salt redox systems or other poorly soluble or unstable drugs of various types, including anticonvulsants.

In related literature, the present inventor and his coworkers have very recently described, in Brewster et al, *J. Pharm. Sci.*, Vol. 80, No. 4, Apr. 1991, 380–383, the development of aqueous parenteral formulation for carbamazepine through the use of modified cyclodextrins. The Brewster et al publication is incorporated by reference herein in its entirety and relied upon. In that publication, the authors note that no intravenous formulation of carbamazepine is currently available, due to the drug's extremely poor water solubility. This makes monotherapy, which is the method of choice in treating convulsive disorders, not possible with carbamazepine when a parenteral form is required, e.g. in pediatric and emergency medicine and in managing the epileptic surgical patient. Accordingly, the ability of various cyclodextrins to enhance the aqueous solubility of carbamazepine was examined in the Brewster et al publication. Dimethyl-$\beta$-cyclodextrin, hydroxypropyl-$\beta$-cyclodextrin, hydroxyethyl-$\beta$-cyclodextrin, $\gamma$-cyclodextrin and hydroxypropyl-$\gamma$-cyclodextrin were all found to significantly enhance the water solubility of carbamazepine. Further testing of carbamazepine solubilized in hydroxypropyl-$\beta$-cyclodextrin showed good stability and potent anticonvulsant effects in both mice and rats when administered intravenously.

CIBA-GEIGY AG's European Patent Publication No. 0435826, published Jul. 3, 1991, describes an aqueous intravenous solution of carbamazepine or oxcarbazepine for use in treating status epilepticus. The aqueous solubility of the drug is enhanced by means of a hydrophilic $C_1$-$C_6$ alkyl, carboxy $C_1$-$C_6$ alkyl, $C_1$-$C_6$ alkoxycarbonyl $C_1$-$C_6$ alkyl and/or hydroxy $C_2$-$C_6$ alkyl γ-cyclodextrin derivative. 2-Hydroxypropyl-, 3-hydroxypropyl- and 2-hydroxyethyl-γ-cyclodextrin are specifically disclosed.

CIBA-GEIGY AG's European Patent Publication No. 0400609, published Dec. 5, 1990, describes an aqueous intravenous solution of carbamazepine in which the drug's aqueous solubility is enhanced by means of $C_1$-$C_4$ alkyl and/or hydroxy-$C_2$-$C_4$ alkyl derivatives of β-cyclodextrin. 2-Hydroxypropyl-β-cyclodextrin and 3-hydroxypropyl-β-cyclodextrin are specifically disclosed.

The Brewster et al publication and that of EP 0435826 and EP 0400609 are limited to parenteral formulations and are, moreover, less than one year prior to the filing date of the present application. At any rate, it has not been recognized by others that the available commercial oral formulations of carbamazepine could be substantially and indeed surprisingly improved upon, in terms of oral bioavailability, through the use of selected cyclodextrin derivatives.

SUMMARY AND OBJECTS OF THE INVENTION

One object of the present invention is to provide a method for improving the oral bioavailability of carbamazepine.

Another object of the present invention is to provide pharmaceutical compositions for oral administration adapted for use in the aforenoted method.

Yet another object of the present invention is to provide improvements in the oral treatment of epilepsy and trigeminal neuralgia.

Another object of the present invention is to provide a method for providing effective treatment of convulsive disorders and neuralgia at lower oral dosage levels (individual and/or daily) than possible with formulations of carbamazepine which are currently commercially available.

Still another object of the present invention is to provide increased and less variable blood levels of carbamazepine than possible with currently available oral dosage forms.

Another object of the present invention is to provide a method and oral dosage forms capable of achieving therapeutic blood levels more rapidly than possible with current oral formulations of carbamazepine.

Still another object of the present invention is to provide a method and compositions for use in the emergency treatment of grand mal status epilepticus seizures.

Yet another object of the present invention is to provide an acceptable alternative for patients, e.g. children, who are unable to swallow tablets.

Another object of the present invention is to provide a sustained-release oral dosage form of carbamazepine in which the rate of release is not controlled by the drug's solubility.

The foregoing objects are achieved in accord with the present invention by means of methods and compositions utilizing complexes of carbamazepine with cyclodextrin selected from the group consisting of hydroxypropyl and hydroxyethyl derivatives of β- and γ-cyclodextrin.

Thus, in one aspect, the present invention provides a method for improving the oral bioavailability of carbamazepine by administering per os, to a warm-blooded animal in need of carbamazepine therapy, particularly in the treatment of convulsive disorders and neuralgia, a therapeutically effective amount of carbamazepine complexed with cyclodextrin selected from the group consisting of hydroxypropyl and hydroxyethyl derivatives of β- and γ-cyclodextrin.

In another aspect, the present invention provides a method for improving the oral bioavailability of carbamazepine by administering per os, to a warm-blooded animal in need of carbamazepine therapy, particularly in the treatment of convulsive disorders and neuralgia, a therapeutically effective amount of carbamazepine in an aqueous solution comprising from about 20% to about 50% cyclodextrin selected from the group consisting of hydroxypropyl and hydroxyethyl derivatives of β- and γ-cyclodextrin.

In yet another aspect, the present invention provides a pharmaceutical composition of matter comprising, in unit oral dosage form, a therapeutically effective amount (e.g. an amount effective to treat epilepsy or other convulsive disorder or an amount effective to treat neuralgia) of carbamazepine complexed with cyclodextrin selected from the group consisting of hydroxypropyl and hydroxyethyl derivatives of β- and γ-cyclodextrin; and a non-toxic pharmaceutically acceptable carrier therefor.

In still another aspect, the present invention provides a pharmaceutical composition of matter comprising, in unit oral dosage form, a therapeutically effective amount (e.g. an amount effective to treat epilepsy or other convulsive disorder or an amount effective to treat neuralgia) of carbamazepine in an aqueous solution comprising from about 20% to about 50% cyclodextrin selected from the group consisting of hydroxypropyl and hydroxyethyl derivatives of β- and γ-cyclodextrin.

In another aspect, the present invention provides use of a complex of carbamazepine with cyclodextrin selected from the group consisting of hydroxypropyl and hydroxyethyl derivatives of β- and γ-cyclodextrin, in the preparation of a medicament for oral administration to an animal in need of carbamazepine therapy.

In presently preferred embodiments of the invention, the cyclodextrin is hydroxypropyl-β-cyclodextrin, particularly 2-hydroxypropyl-β-cyclodextrin.

BRIEF DESCRIPTION OF THE DRAWINGS

The aforenoted and other objects and advantages of the present invention will be apparent from the following detailed description and accompanying drawings, in which.

DETAILED DESCRIPTION OF THE INVENTION

The expression "carbamazepine therapy" as used herein is intended to encompass treatment of any and all medical conditions responsive to the drug carbamazepine when administered orally, especially treatment of convulsive disorders and neuralgia. Moreover, the word "treatment" used in this context is intended to include not only administration to alleviate convulsions and/or the pain of trigeminal neuralgia, but also use in the prevention of convulsions and neuralgia. Prophylactic treatment of convulsive disorders is in fact the method of choice, the object being to maintain patients prone to convulsions on anticonvulsive medication at a level sufficient to prevent convulsions from occurring.

Carbamazepine for use in the methods and compositions of the present invention is commercially available. Alternatively, it may be synthesized by well-known methods, for example, that of Schindler U.S. Pat. No. 2,948,718.

The cyclodextrins contemplated for use herein are hydroxypropyl and hydroxyethyl derivatives of $\beta$-cyclodextrin, and hydroxypropyl and hydroxyethyl derivatives of $\gamma$-cyclodextrin. The hydroxyalkyl groupings may contain one or more hydroxyl groups, e.g. hydroxypropyl (2-hydroxypropyl, 3-hydroxypropyl), dihydroxypropyl and the like. Various mixtures of the cyclodextrin derivatives may be used as well. A presently preferred cyclodextrin derivative is 2-hydroxypropyl-$\beta$-cyclodextrin, also referred to hereinbelow as HP$\beta$CD.

Hydroxypropyl and hydroxyethyl derivatives of $\beta$- and $\gamma$-cyclodextrin are commercially available or can be prepared by known methods. See, for example, the preparative methods discussed in Bodor U.S. Pat. No. 5,024,998, issued Jun. 18, 1991, and Brewster et al, *J. Pharm. Sci.*, Vol, 80, No. 4, Apr. 1991, 380–383, both of which are incorporated by reference herein in their entireties. Preparation of solutions of carbamazepine (CBZ) containing 20, 30, 40 and 50 w/v (0.13–0.32M) HP$\beta$CD and preparation of a solid CBZ/HP$\beta$CD complex eminently suitable for use herein are also detailed in the Brewster et al publication.

In order to determine to what extent, if any, the oral bioavailability of carbamazepine could be improved through complexation with a cyclodextrin derivative as defined herein, the following pharmacokinetic study in dogs of a solution of a CBZ/HP$\beta$CD complex in comparison with a commercially available immediate-release carbamazepine tablet was undertaken.

MATERIALS AND METHODS

Materials

Carbamazepine (CBZ) for the complex and analytical standard was obtained from Sigma Chemical Co., St. Louis, Mo. The HP$\beta$CD and the complex were prepared as described by Brewster et al, *J. Pharm. Sci.*, Vol. 80, No. 4, Apr. 1991, 380–383. The HP$\beta$CD solution was made using deionized water (Barnstad Nanopure II Ultrapure Water System). An excess of CBZ was sonicated in the HP$\beta$CD solution for 24 hours at room temperature. The resulting suspension was centrifuged and filtered through 0.45 μm polyvinylidine difluoride membranes (Millex, HV4, Millipore). The filtrate was frozen in liquid nitrogen and lyophilized (Labconco Model 18 Freeze-Drier). The solid was then milled and passed through a 60 mesh sieve. The degree of drug incorporation in the HP$\beta$CD/CBZ complex was determined by HPLC to be 58.8 mg CBZ per gram of HP$\beta$CD/CBZ complex. Stoichiometrically, this corresponds to a system containing approximately 2.6 molecules of HP$\beta$CD per CBZ structure, as depicted below.

CARBAMAZEPINE $R = [(CH_2CH(OH)CH_2)]_n H$
$n = 0, 1, 2 \ldots$ (Phase solubility studies of aqueous solutions of CBZ with up to 50% w/v HP$\beta$CD detailed by Brewster et al suggest formation of a 1:1 CBZ-HP$\beta$CD complex in dilute HP$\beta$CD solutions and a high order (1:2) complex in more concentrated solutions.)

For the analytical procedure, carbamazepine-10,11-epoxide standard was purchased from Alltech Associated, State College, Pa. The internal standard, tolybarb (5-ethyl-5-p-tolylbarbituric acid), was purchased from Aldrich Chemical Co., Inc., Milwaukee, Minn. Methanol, acetonitrile and methylene chloride were HPLC quality and were purchased from American Burdick and Jackson, Muskegan, Mich. All other reagents were of reagent grade quality. Buffers were prepared using deionized water which had been passed through a MilliQ purification system. All buffers used in the HPLC mobile phase were filtered through a 0.45 μm filter (Millipore Corp., Bedford, Mass.).

In Vivo Study Design

A two-way crossover, randomized study in 6 beagle dogs (3 males and 3 females) was carried out in which the treatments were as follows: carbamazepine tablets (Tegretol ® 200 mg Tablets, Geigy Pharmaceuticals) dosed fasting and with 45 mL of deionized water; and the HP$\beta$CD/CBZ complex dosed fasting. The dose for both treatments consisted of 200 mg of carbamazepine. The 3.28 g HP$\beta$CD/CBZ complex was dissolved in 25 mL of deionized water (at room temperature). This solution was administered to the fasting dogs by gavage within 10 minutes after its dissolution. The complex was completely dissolved and formed a clear solution. The bottle that contained the complex was washed with two consecutive 10 mL quantities of deionized water and administered to the dogs by gavage.

Serial blood samples were drawn via a venous catheter at 0, 0.25, 0.5, 0.75, 1.0, 1.25, 1.5, 1.75, 2.0, 3.0, 4.0, 5.0, 6.0, 8.0, 12.0 and 24.0 hours after the dose. Plasma samples were analyzed in duplicate for carbamazepine by a fully validated high pressure liquid chromatography (HPLC) method.

Analytical

The CBZ and internal standard (tolybarb) were extracted from plasma using solid phase extraction columns. Extraction columns (ClinElut, size CE1001, Analytichem International, Harbor City, Calif.) were placed over 16×85 mm disposable glass centrifuge tubes. The columns were preconditioned with a 1 M potassium phosphate buffer, pH 6.8. The 100 μL of the internal standard (5 μg/mL tolybarb) was added to the top of the column and then 200 μL of plasma sample was added. The column was allowed to equilibrate for 5 minutes. After this equilibration step, 10 mL of methylene chloride was added and the effluent was collected in glass tubes. A total of approximately 9.0 mL of the methylene chloride was recovered from each extraction. The effluent was evaporated from the tube at 50° C. under a stream of nitrogen. The residue was reconstituted with 50 μL of methanol and placed in a microinjection vial for injection into the HPLC.

The method used to detect and quantitate the plasma CBZ was a modification of a method described by Ou et al, *Clin. Chem.* 30: 1667–1670 (1984). The liquid chromatograph used a Waters M600 isocratic system equipped with an automatic injector (712 WISP, Waters Chromatography, Milford, Mass.) and a radial compression module with a 8 mm × 10 cm Nova-Pak 4 micron ODS cartridge (RCM-100, Waters Chromatography, Milford, Mass.) and a variable wavelength UV detector (Model 490, Waters Chromatography, Milford, Mass.). The mobile phase consisted of methanol : acetonitrile : 25 mM potassium phosphate buffer, pH 7.0 (10:30:60) which was premixed and degassed using sonication and vacuum. The flow rate was 2.0 mL per minute. Detection of CBZ and internal standard was by UV absorption at 210 nm. Retention times of tolybarb and CBZ were 4.1 and 5.9 minutes, respectively. Carbamazepine-10,11-epoxide was separated from CBZ (retention time = 3.3 minutes) but was not quantified. Injection volume was 10 μL. The absorption was recorded using a recording integrator (Model 3392, Hewlett Packard, Avondale, Pa.) and quantification was based on peak height measurements.

Standard curves were developed using canine plasma for the range of 0.33 to 5.0 μg/mL CBZ. The method was linear between this range of concentrations ($r^2 = 0.9996$). The precision data were obtained from replicate determinations at 2.5 μg/mL. Within-run coefficient of variations (CVs) were < 6.0% and between-run CVs were < 4.2%.

Pharmacokinetic Analysis

The carbamazepine concentration-time data was evaluated for the extent and rate of carbamazepine absorption. Area under the curve to the last time point (AUC24) was calculated by using the log-linear trapezoidal rule to the last time point. The AUCinf was not calculated because elimination rate constants could not be calculated from the Tegretol data. The ratio of the AUC24 for the complex to the AUC24 for Tegretol was used to evaluate the extent of absorption. The maximum plasma concentration (Cmax) and the ratio of the Cmax values were also used to evaluate the extent of absorption. The time to the maximum concentration (tmax) and its ratio were used to evaluate the rate of absorption. The elimination rate (or terminal rate) constant (K) could only be calculated for the complex. The data was analyzed statistically using a paired t-test.

RESULTS AND DISCUSSION

Figure 1:
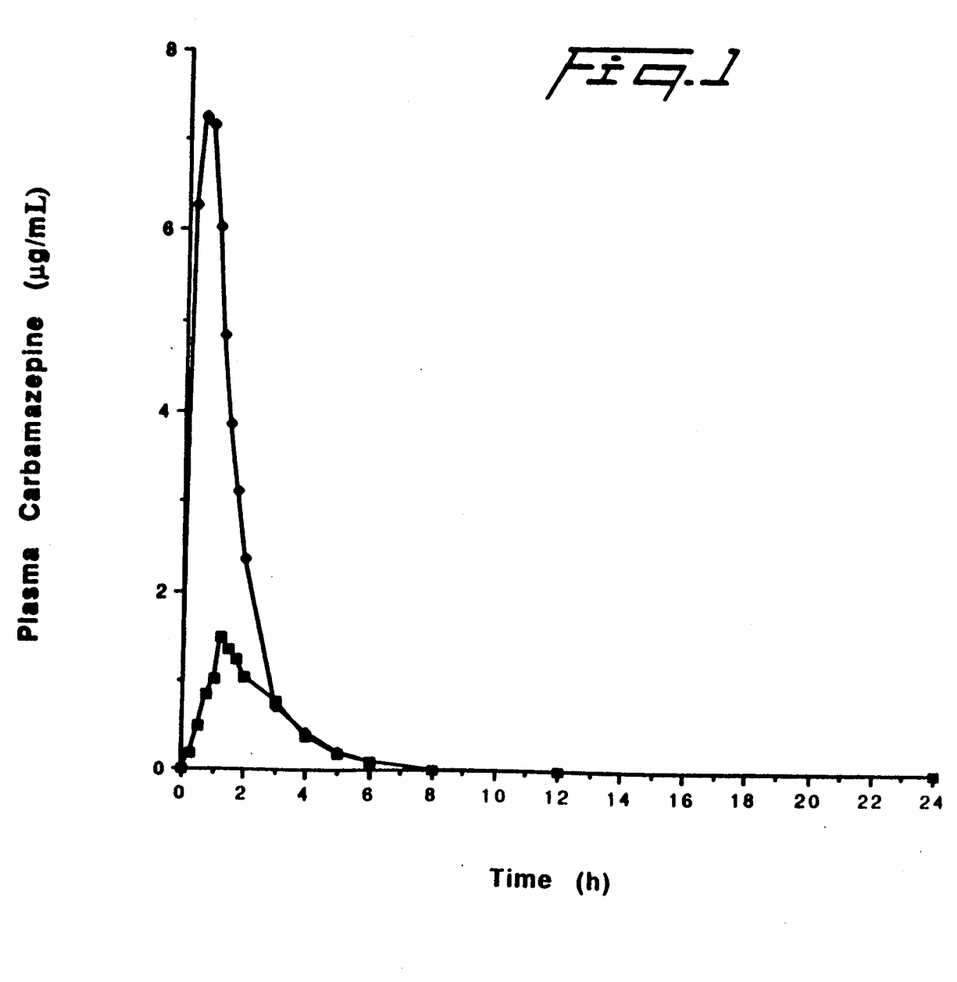
FIG. 1 is a plot of mean plasma carbamazepine levels in μg/mL against time in hours following oral administration of a single dose of Tegretol ® brand 200 mg carbamazepine tablets (-□-) and a single dose of carbamazepine/2-hydroxypropyl-β-cyclodextrin complex containing 200 mg carbamazepine (-■-) to a group of six beagle dogs.
Figure 2:
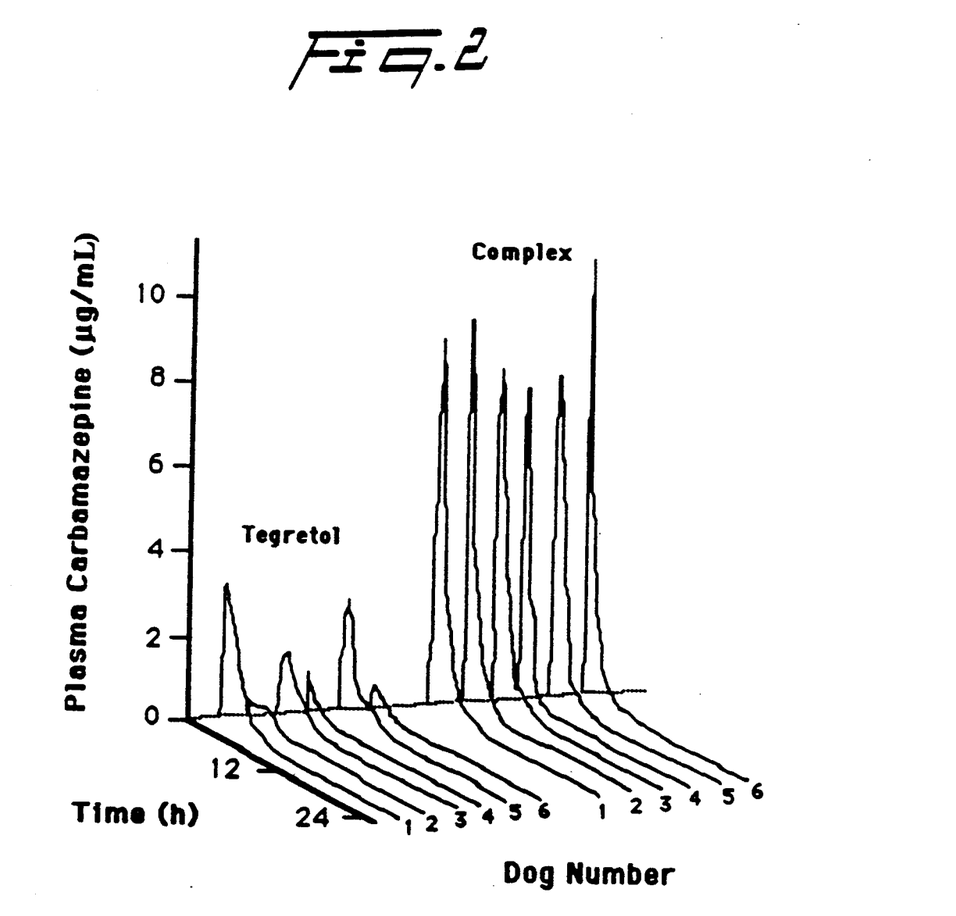
FIG. 2 is a graph of the individual plasma carbamazepine levels in μg/mL against time in hours following a single dose of Tegretol ® brand 200 mg carbamazepine tablets and a single dose of carbamazepine/2-hydroxypropyl-β-cyclodextrin complex containing 200 mg carbamazepine for each of six beagle dogs.

Carbamazepine was significantly better absorbed from the HPβCD/CBZ complex than from the CBZ tablet as is illustrated in FIG. 1 and Table I. The individual dogs and treatments are graphed in FIG. 2.

TABLE I

| | Mean and Individual Pharmacokinetic Data | | | | | | | | |
|---|---|---|---|---|---|---|---|---|---|
| | TEGRETOL (T) | | | HPβCD/CBZ complex (C) | | | RATIO (C/T) | | |
| Dog # | AUC (μg · h/mL) | Cmax (μg/mL) | tmax (h) | AUC (μg · h/mL) | Cmax (μg/mL) | tmax (h) | AUC (μg · h/mL) | Cmax (μg/mL) | tmax (h) |
| 1 | 7.97 | 3.25 | 1.25 | 14.82 | 8.59 | 0.75 | 1.97 | 2.64 | 0.60 |
| 2 | 1.82 | 0.54 | 3.00 | 15.31 | 8.94 | 0.50 | 7.43 | 16.71 | 0.17 |
| 3 | 4.26 | 1.60 | 1.50 | 14.18 | 7.77 | 0.75 | 3.45 | 4.84 | 0.50 |
| 4 | 0.98 | 0.92 | 0.50 | 7.68 | 7.23 | 0.25 | 7.47 | 7.86 | 0.50 |
| 5 | 5.84 | 2.62 | 1.00 | 11.71 | 7.40 | 0.50 | 1.79 | 2.82 | 0.50 |
| 6 | 1.15 | 0.59 | 1.00 | 13.26 | 10.12 | 0.25 | 11.56 | 17.04 | 0.25 |
| Mean | 3.67 | 1.59 | 1.38 | 12.83 | 8.34 | 0.50 | 5.61 | 8.65 | 0.42 |
| S.D. | 2.85 | 1.13 | 0.56 | 2.82 | 1.10 | 0.22 | 3.86 | 6.64 | 0.17 |
| CV % | 78 | 71 | 62 | 22 | 13 | 44 | 69 | 77 | 44 |
| Median | 3.04 | 1.26 | 1.13 | 13.72 | 8.18 | 0.50 | 5.44 | 6.35 | 0.50 |

The mean ratio of the HPβCD/CBZ complex AUC to the tablet AUC was found to be 5.61 (range: 1.79 to 7.47). In addition, the coefficient of variation around the HPβCD/CBZ complex AUC was considerably tighter (22%) than the tablet AUC (78%). The AUC for the HPβCD/CBZ complex was significantly greater ($p<0.01$) than the tablet. The more than 5-fold mean increase in the AUC was completely unexpected and surprising. An up to about 30% increase was anticipated as the maximum improvement attainable based on the 75-85% oral bioavailability for commercial formulations described in the carbamazepine art. Thus, the present invention provides an approximately 19-fold greater improvement in oral bioavailability than the art considered was the maximum improvement possible for any oral formulation.

The increased extent of absorption and increased reproducibility of the AUC values from the HPβCD/CBZ complex may be partially due to the increased water solubility of the complex, but are believed to be primarily due to the increased rate of in vivo dissolution of the complex versus micronized carbamazepine following oral administration, a rate which could not be predicted.

The terminal rate constant of CBZ was $0.997 \pm 0.389$ hours for the HP$\beta$CD/CBZ complex. Because of slow release of CBZ from the conventional tablet and low plasma CBZ levels, the terminal rate constant could not be calculated from the tablet data.

The rapid rate of dissolution of the CBZ/HP$\beta$CD complex allowed the CBZ to be absorbed significantly faster than the CBZ in the tablet as is illustrated in the significantly shorter tmax (p=0.0481), 1.38 hours and 0.50 hour for Tegretol® and HP$\beta$CD/CBZ complex, respectively. The accelerated rate and greater extent of absorption combined to produce a large increase (p<0.01) in the Cmax values from the HP$\beta$CD/CBZ complex. The mean Cmax increased from 1.59 $\mu$g/mL (CV=71%) for Tegretol® to 8.34 $\mu$g/mL (CV=13%) for the HP$\beta$CD/CBZ complex. The low variability of the HP$\beta$CD/CBZ complex data is reflected in the Cmax data.

It would appear that from this data the rate of dissolution of CBZ from conventional tablets is the rate-limiting step for the absorption of the drug in the dog. Complexing CBZ with HP$\beta$CD permits the rate-limiting step to shift to the process of absorption through the gut wall. Because of this, there is a greater extent of absorption, a much faster rate and a less variable kinetic profile for the CBZ from the HP$\beta$CD/CBZ complex.

Carbamazepine is known to be effective against maximal electroshock seizure (MES) test models. MES testing is in fact a cornerstone for detecting and quantitating anticonvulsant activity in drugs of this type. The anticonvulsant effects of oral administration of the carbamazepine/hydroxypropyl-$\beta$-cyclodextrin complex and other complexes of the present invention can be confirmed in MES testing, for example, in tests of the type described by Brewster et al, *J. Pharm. Sci.*, Vol. 80, No. 4, Apr. 1991, 380–383. Other appropriate tests of the oral administration of the instant complexes are those tests in which carbamazepine itself is active.

From the foregoing, it can be seen that the present invention provides a method for improving the oral bioavailability of carbamazepine by administering per os, to a warm-blooded animal in need of carbamazepine therapy, a therapeutically effective amount of carbamazepine complexed with cyclodextrin selected from the group consisting of hydroxypropyl and hydroxyethyl derivatives of $\beta$- and $\gamma$-cyclodextrin. The complex may be orally administered per se; to that end, for example, the complex may simply be compressed into tablets. However, it is frequently convenient or desirable to administer the complex in an aqueous oral solution or syrup comprising from about 20% to about 50% w/w or w/v selected cyclodextrin. The liquid oral formulation may, if desired, contain various excipients in addition to the aqueous carrier, particularly coloring, flavoring and/or sweetening agents. Alternatively, the complex may be formulated into a solid oral dosage form. Thus, it may be combined with one or more carriers or excipients, including diluents, binders, glidants, lubricants, disintegrants, colors, flavors and sweetening agents and compressed into tablets or caplets or filled into capsules. Pills, powders and granules may be similarly prepared. The solid oral dosage forms, particularly the tablets and caplets, may be sugar coated, film coated, enteric coated, layered or they may be in sustained release form, e.g. of the osmotic or of the microencapsulated form. Sustained release formulations are of particular interest.

Appropriate excipients for use in and methods for the formulation of the oral dosage forms of the present invention will be apparent to those of ordinary skill in the art. See, for example, *Remington's Pharmaceutical Sciences*, seventeenth edition, ed. Alfonso R. Gennaro, Mack Publishing Company, Easton, Pa. (1985), especially Chapters 84, 90, 91 and 92.

Because of the vastly improved oral bioavailability provided by the present invention, carbamazepine administered orally as the instant complex can be administered at much lower daily dosage levels than heretofore possible for oral administration of carbamazepine itself. Maintenance dosage levels as low as 150–350 mg daily are currently envisioned for adults suffering from convulsive disorders. Effective oral treatment of epilepsy and trigeminal neuralgia at considerably lower oral dosage levels (individual and/or daily) than currently available is thus contemplated. Moreover, at comparable dosage levels to current oral formulations, greatly increased blood levels of carbamazepine may be obtained. Thus, it should be possible to select a lower dosage level which will nevertheless provide higher blood levels of carbamazepine. Based on the test results detailed hereinabove, therapeutic blood levels are also less variable and are achieved more rapidly herein than possible with current oral formulations. Use of a sustained-release oral formulation in accord with the present invention could provide therapeutic blood levels of carbamazepine over extended periods of time without undesirable fluctuations and with a lower incidence of side effects. No sustained release formulations of carbamazepine have been possible heretofore.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims, and equivalents thereof.

What is claimed is:

1. A method for improving the oral bioavailability of carbamazepine, said method comprising administering per os, to a warm-blooded animal in need of carbamazepine therapy, a therapeutically effective amount of carbamazepine complexed with cyclodextrin selected from the group consisting of hydroxypropyl and hydroxyethyl derivatives of $\beta$- and $\gamma$-cyclodextrin.

2. The method according to claim 1, wherein the complex comprises at least 2 molecules of cyclodextrin per molecule of carbamazepine.

3. The method according to claim 1, wherein the cyclodextrin comprises hydroxypropyl-$\beta$-cyclodextrin.

4. The method according to claim 3, wherein the complex comprises at least 2 molecules of hydroxypropyl-$\beta$-cyclodextrin per molecule of carbamazepine.

5. The method according to claim 4, wherein the complex comprises between 2 and 3 molecules of hydroxypropyl-$\beta$-cyclodextrin per molecule of carbamazepine.

6. The method according to claim 1, wherein the animal is in need of carbamazepine therapy for a convulsive disorder, and an effective anticonvulsant amount of carbamazepine is administered.

7. The method according to claim 1, wherein the animal is in need of carbamazepine therapy for neuralgia and an effective antineuralgic amount of carbamazepine is administered.

8. A method for improving the oral bioavailability of carbamazepine, said method comprising administering per os, to a warm-blooded animal in need of carbamazepine therapy, a therapeutically effective amount of carbamazepine in an aqueous solution comprising from about 20% to about 50% cyclodextrin selected from the group consisting of hydroxypropyl and hydroxyethyl derivatives of β- and γ-cyclodextrin.

9. The method according to claim 8, wherein said aqueous solution is prepared from a complex of carbamazepine with cyclodextrin selected from the group consisting of hydroxypropyl and hydroxyethyl derivatives of β- and γ-cyclodextrin.

10. The method according to claim 9, wherein the complex comprises at least 2 molecules of cyclodextrin per molecule of carbamazepine.

11. The method according to claim 8, wherein the cyclodextrin comprises hydroxypropyl-β-cyclodextrin.

12. The method according to claim 9, wherein the cyclodextrin comprises hydroxypropyl-β-cyclodextrin.

13. The method according to claim 12, wherein the complex comprises at least 2 molecules of hydroxypropyl-β-cyclodextrin per molecule of carbamazepine.

14. The method according to claim 13, wherein the complex comprises between 2 and 3 molecules of hydroxypropyl-β-cyclodextrin per molecule of carbamazepine.

15. The method according to claim 8, wherein the animal is in need of carbamazepine therapy for a convulsive disorder, and an effective anticonvulsant amount of carbamazepine is administered.

16. The method according to claim 8, wherein the animal is in need of carbamazepine therapy for neuralgia, and an effective antineuralgic amount of carbamazepine is administered.

17. A pharmaceutical composition of matter comprising, in unit oral dosage form, a therapeutically effective amount of carbamazepine complexed with cyclodextrin selected from the group consisting of hydroxypropyl and hydroxyethyl derivatives of β- and γ-cyclodextrin; and a non-toxic pharmaceutically acceptable carrier therefor.

18. The composition according to claim 17, formulated as a solid oral dosage form.

19. The composition according to claim 18, formulated as a tablet, caplet or capsule.

20. The composition according to claim 17, formulated as a sustained release oral dosage form.

21. The composition according to claim 17, wherein the complex comprises at least 2 molecules of cyclodextrin per molecule of carbamazepine.

22. The composition according to claim 17, wherein the cyclodextrin comprises hydroxypropyl-β-cyclodextrin.

23. The composition according to claim 22, wherein the complex comprises at least 2 molecules of hydroxypropyl-β-cyclodextrin per molecule of carbamazepine.

24. The composition according to claim 23, wherein the complex comprises between 2 and 3 molecules of hydroxypropyl-β-cyclodextrin per molecule of carbamazepine.

25. The composition according to claim 17, wherein the therapeutically effective amount of carbamazepine is an effective anticonvulsant amount.

26. The composition according to claim 17, wherein the therapeutically effective amount of carbamazepine is an effective antineuralgic amount.

27. A pharmaceutical composition of matter comprising, in unit oral dosage form, a therapeutically effective amount of carbamazepine in an aqueous solution comprising from about 20% to about 50% cyclodextrin selected from the group consisting of hydroxypropyl and hydroxyethyl derivatives of β- and γ-cyclodextrin.

28. The composition according to claim 27, wherein said aqueous solution is prepared from a complex of carbamazepine with cyclodextrin selected from the group consisting of hydroxypropyl and hydroxyethyl derivatives of β- and γ-cyclodextrin.

29. The composition according to claim 28, wherein the complex comprises at least 2 molecules of cyclodextrin per molecule of carbamazepine.

30. The composition according to claim 27, wherein the cyclodextrin comprises hydroxypropyl-β-cyclodextrin.

31. The composition according to claim 28, wherein the cyclodextrin comprises hydroxypropyl-β-cyclodextrin.

32. The composition according to claim 31, wherein the complex comprises at least 2 molecules of hydroxypropyl-β-cyclodextrin per molecule of carbamazepine.

33. The composition according to claim 32, wherein the complex comprises between 2 and 3 molecules of hydroxypropyl-β-cyclodextrin per molecule of carbamazepine.

34. The composition according to claim 27, wherein the therapeutically effective amount of carbamazepine is an effective anticonvulsant amount.

35. The composition according to claim 27, wherein the therapeutically effective amount of carbamazepine is an effective antineuralgic amount.

* * * * *